(12) United States Patent
Coffin

(10) Patent No.: US 7,811,582 B2
(45) Date of Patent: *Oct. 12, 2010

(54) HERPES VIRUSES FOR IMMUNE MODULATION

(75) Inventor: Robert S. Coffin, London (GB)

(73) Assignee: Biovex Limited, Oxford (GB)

( * ) Notice: Subject to any disclaimer, the term of this patent is extended or adjusted under 35 U.S.C. 154(b) by 676 days.

This patent is subject to a terminal disclaimer.

(21) Appl. No.: 11/333,309

(22) Filed: Jan. 18, 2006

(65) Prior Publication Data

US 2006/0121522 A1    Jun. 8, 2006

Related U.S. Application Data

(63) Continuation of application No. 10/766,897, filed on Jan. 30, 2004, now Pat. No. 7,118,755, which is a continuation-in-part of application No. 09/833,073, filed on Apr. 12, 2001, now Pat. No. 6,713,067, which is a continuation-in-part of application No. 09/744,942, filed as application No. PCT/GB99/02529 on Aug. 2, 1999, now Pat. No. 6,641,817.

(30) Foreign Application Priority Data

| Jul. 31, 1998 | (GB) | ................................. 9816781.0 |
| Apr. 12, 2000 | (GB) | ................................. 0009079.5 |

(51) Int. Cl.
*A61K 39/245* (2006.01)
*C12N 7/00* (2006.01)
*C12N 7/04* (2006.01)

(52) U.S. Cl. ............... 424/231.1; 424/204.1; 424/205.1; 435/235.1; 435/236

(58) Field of Classification Search .................. None
See application file for complete search history.

(56) References Cited

U.S. PATENT DOCUMENTS

| 5,998,174 | A | 12/1999 | Glorioso et al. |
| 6,641,817 | B1 | 11/2003 | Coffin |
| 6,713,067 | B2 * | 3/2004 | Coffin ..................... 424/199.1 |

FOREIGN PATENT DOCUMENTS

| WO | WO 97/13866 | 4/1997 |
| WO | WO 98/04726 | 2/1998 |
| WO | WO 98/30707 | 7/1998 |
| WO | WO 98/51809 | 11/1998 |
| WO | WO 99/60145 | 11/1999 |
| WO | WO 00/08191 | 2/2000 |

OTHER PUBLICATIONS

Krisky et al. Development of herpes simplex virus replication defective multigene vectors for combination gene therapy applications. Gene Therapy, Nov. 1998, vol. 5, No. 11, pp. 1517-1530.*

Coffin et al. Pure populations of transduced primary human cells can be produced using GFP expressing herpes virus vectors and flow cytometry. Gene Therapy, May 1998, vol. 5, No. 5, pp. 718-722.*

Ace et al. "Construction and characterization of a herpes simplex virus type 1 mutant unable to transinduce immediate-early gene expression" J. Virol. 63:2260-2269 (1989).

Aicher et al. "Successful retroviral mediated transduction of a reporter gene in human dendritic cells: Feasibility of therapy with gene-modified antigen presenting cells" Exp. Hematol. 25:39-44 (1997).

Arthur et al. "A comparison of gene transfer methods in human dendritic cells" Cancer Gene Therapy 4:17-25 (1997).

Caux et al. "GM-CSF and TNF-α cooperate in the generation of dendritic Langerhans cells" Nature 360:258-261 (1992).

Celluzzi et al. "Peptide-pulsed dendritic cells induce antigen-specific, CTL-mediated protective tumor immunity" J. Exp. Med. 183:283-287 (1996).

Chou et al. "Differential response of human cells to deletions and stop codons in the $_{\gamma_1}34.5$ gene of herpes simplex virus" J. Virol. 68:8304-8311 (1994).

Chou et al. "The $_{\gamma_1}34.5$ gene of herpes simplex virus 1 precludes neuroblastoma cells from triggering total shutoff of protein synthesis characteristics of programmed cell death in neuronal cells" Proc. Natl. Acad. Sci. USA 89:3266-3270 (1992).

Coffin et al. "Herpes simplex virus-based vectors" in *Gene Manipulation of the Nervous System* (Latchman, ed.), Academic Press, Chapter 6, pp. 100-114 (1995).

Coffin et al. "Gene delivery to the central and peripheral nervous systems of mice using HSV1 ICP34.5 deletion mutant vectors" Gene Therapy 3:886-891 (1996).

Coffin et al. "Pure populations of transduced primary human cells can be produced using GFP expressing herpes virus vectors and flow cytometry" Gene Therapy 5:718-722 (1998).

(Continued)

*Primary Examiner*—Zachariah Lucas
(74) *Attorney, Agent, or Firm*—Nixon & Vanderhye P.C.

(57) ABSTRACT

An attenuated herpes virus which lacks a functional vhs gene or a functional equivalent thereof, but which has a functional UL43 gene or functional equivalent thereof, stimulates an immune response when dendritic cells are infected with the virus.

19 Claims, 5 Drawing Sheets

OTHER PUBLICATIONS

Figure 1:
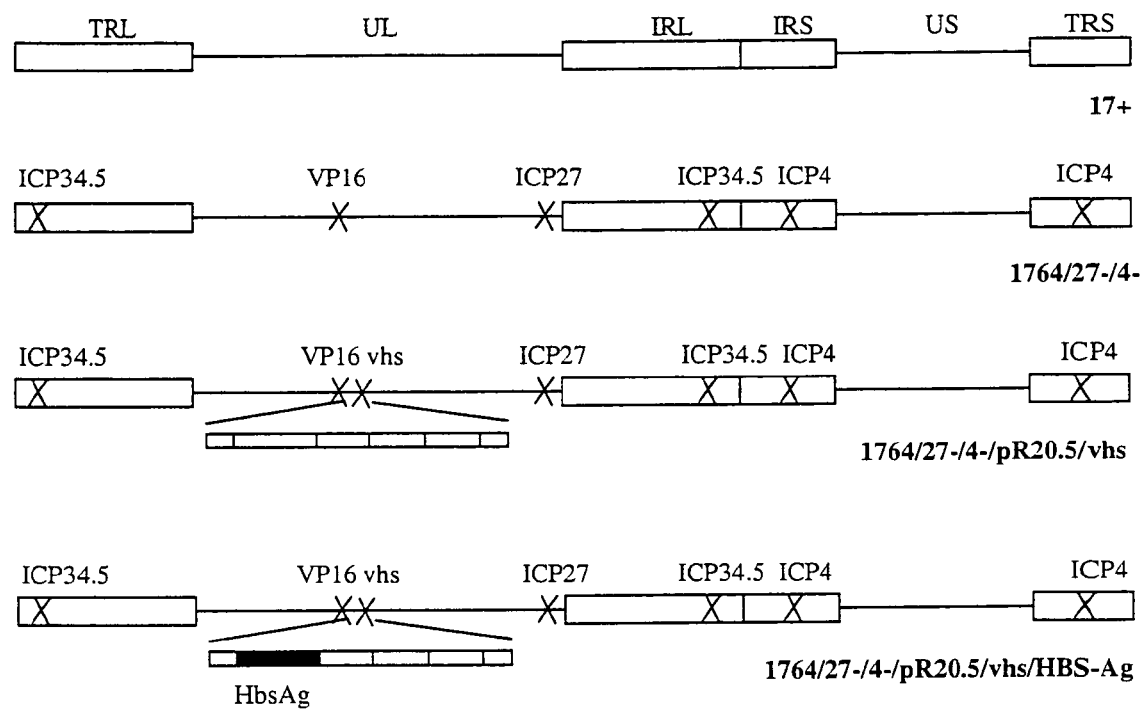

DeLuca et al. "Isolation and characterization of deletion mutants of herpes simplex virus type 1 in the gene encoding immediate-early regulatory protein ICP4" J. Virol. 56:558-570 1985.

Dilloo et al. "A novel herpes vector for the high-efficiency transduction of normal and malignant human hematopoietic cells" Blood 89:119-127 (1997).

Geiss et al. "Disruption of virion host shutoff activity improves the immunogenicity and protective capacity of a replication-incompetent herpes simplex virus type 1 vaccine strain" J. Virol. 74:111137-11144 (2000).

Gendler et al. "Molecular cloning and expression of human tumor-associated polymorphic epithelial mucin" J. Biol. Chem. 265:15286-15293 (1990).

Girolomoni et al. "Dendritic cells hold promise for immunotherapy" Immunology Today 18:103-104 (1997).

Goldsmith et al. "Infected Cell Protein (ICP)47 enhances herpes simplex virus neurovirulence by blocking the CD8 T cell response" J. Exp. Med. 187:341-348 (1998).

Gossen et al. "Tight control of gene expression in mammalian cells by tetracycline-responsive promoters" Proc. Natl. Acad. Sci. USA 89:5547-5551 (1992).

Gough et al. "Expression of the hepatitis B virus surface, core and E antigen genes by stable rat and mouse cell lines" J. Mol. Biol. 162:43-67 (1982).

Huard et al. "Gene transfer to muscle using herpes simplex virus-based vectors" Neuromuscular Disorders 7:299-313 (1997) (Abstract only cited).

Inaba et al. "Identification of proliferating dendritic cell precursors in mouse blood" J. Exp. Med. 175:1157-1167 (1992).

Jones et al. "Mutational analysis of the herpes simplex virus virion host shutoff protein: Evidence that vhs functions in the absence of other viral proteins" J. Virol. 69:4863-4871 (1995).

Krisky et al. "Development of herpes simplex virus replication-defective multigene vectors for combination gene therapy applications" Gene Therapy 5:1517-1530 (1998).

Kruse et al. "Mature dendritic cells infected with herpes simplex virus type 1 exhibit inhibited T-cell stimulatory capacity" J. Virol. 74:7127-7136 (2000).

Lokensgard et al. "Long-term promoter activity during herpes simplex virus latency" J. Virol. 68:7148-7158 (1994).

MacLean et al. "Herpes simplex virus type 1 deletion variants 1714 and 1716 pinpoint neurovirulence-related sequences in Glasgow strain 17 between immediate early gene 1 and the 'a' sequence" J. Gen. Virol. 72:631-639 (1991).

MacLean et al. "Investigation of herpes simplex virus type 1 genes encoding multiply inserted membrane proteins" J. Gen. Virol. 72:897-906 (1991).

McFarlane et al. "Hexamethylene bisacetamide stimulates herpes simplex virus immediate early gene expression in the absence of trans-induction by Vmw65" J. Gen. Virol. 73:285-292 (1992).

Reeves et al. "Retroviral transduction of human dendritic cells with a tumor-associated antigen gene" Cancer Research 56:5672-5677 (1996).

Rice et al. "Genetic evidence for two distinct transactivation functions of the herpes simplex virus α protein ICP27" J. Virol. 64:1704-1715 (1990).

Salio et al. "Inhibition of dendritic cell maturation by herpes simplex virus" Eur. J. Immunol. 29:3245-3253 (1999).

Sallusto et al. "Efficient presentation of soluble antigen by cultured human dendritic cells is maintained by granulocyte/macrophage colony-stimulating factor plus interleukin 4 and downregulated by tumor necrosis factor α" J. Exp. Med. 179:1109-1118 (1994).

Samaniego et al. "Functional interactions between herpes simplex virus immediate-early proteins during infection: Gene expression as a consequence of ICP27 and different domains of ICP4" J. Virol. 69:5705-5715 (1995).

Smiley et al. "Truncation of the C-terminal acidic transcriptional activation domain of herpes simplex virus VP16 produces a phenotype similar to that of the in1814 linker insertion mutation" J. Virol. 71:6191-6193 (1997).

Smith et al. "Evidence that the herpes simplex virus immediate early protein ICP27 acts post-transcriptionally during infection to regulate gene expression" Virology 186:74-66 (1992).

Strelow et al. "Role of the virion host shutoff (vhs) of herpes simplex virus type 1 in latency and pathogenesis" J. Virol. 69:6779-6786 (1995).

Thomas et al. "Herpes simplex virus latency-associated transcript encodes a protein which greatly enhances virus growth, can compensate for deficiencies in immediate-early gene expression, and is likely to function during reactivation from virus latency" J. Virol. 73:6618-6625 (1999).

Thompson et al. "Herpes simplex virus neurovirulence and productive infection of neural cells is associated with a function which maps between 0.82 and 0.832 map units on the HSV genome" Virology 172:435-450 (1989).

Wagstaff et al. "Gene transfer using a disabled herpes virus vector containing the EMCV IRES allows multiple gene expression in vitro and in vivo" GeneTherapy 5:1566-1570 (1998).

Walker et al. "Protection from primary infection and establishment of latency by vaccination with a herpes simplex virus type 1 recombinant deficient in the virion host shutoff (vhs) function" Vaccine 16:1-5 (1998).

Walker et al. "Postexposure vaccination with a virion host shutoff defective mutant reduces UV-B radiation-induced ocular herpes simplex virus shedding in mice" Vaccine 16:6-8 (1998).

Zitvogel et al. "Therapy of murine tumors with tumor peptide-pulsed dendritic cells: Dependence on T cells, B7 costimulation, and T helper cell 1-associated cytokines" J. Exp. Med. 183:87-97 (1996).

Collins et al. "Gene therapy meets vaccine development" Trends in Biotechnol. 22:623-626 (2004).

* cited by examiner

HERPES VIRUSES FOR IMMUNE MODULATION

This is a continuation of application Ser. No. 10/766,897, filed Jan. 30, 2004, now U.S. Pat. No. 7,118,755; which is a continuation-in-part of application Ser. No. 09/833,073, filed Apr. 12, 2001, now U.S. Pat. No. 6,713,067; which is a continuation-in-part of application Ser. No. 09/744,942, filed Aug. 8, 2001 now U.S. Pat. No. 6,641,817; which is a U.S. national phase of PCT/GB99/02529, filed Aug. 2, 1999; the entire contents of which are incorporated herein by reference.

FIELD OF THE INVENTION

The present invention relates to attenuated herpes simplex viruses capable of efficiently infecting dendritic cells. It also relates to the use of such viruses in immunotherapy approaches to the treatment of disease.

BACKGROUND TO THE INVENTION

Dendritic cells (DCs) are the most potent antigen presenting cells and are efficient at inducing responses even to antigens to which the immune system has become tolerant. Thus for tumour immunotherapy, in which an immune response is raised against a tumour, the use of DCs may be ideal if they were made to present tumour specific antigens. DCs might also be used to present antigens derived from infectious agents, such as bacteria, viruses or parasites, providing protective or therapeutic vaccines for such diseases. However effective transfer of antigens into DCs for any of these targets has proved the greatest problem with this approach.

To provide a realistic chance of generating a therapeutic immune response against a tumour antigen or other disease related antigen, several conditions have to be met. Firstly, it is necessary to identify molecules whose expression is tumour or disease specific (or at least selective), and which can therefore serve as the target for an immune response. This task has proved very difficult for the majority of common tumours, but is solved in for example the case of cervical cancer by the presence, in most cases, of the viral oncogenes E6 and E7, and for other tumours, good candidate antigens are beginning to be identified. For example the MUC-1 gene product is over expressed in a number of tumours, including 90% of ovarian cancers. Various other tumour associated antigens have also been identified, any of which might be used in an immunotherapy treatment of cancer. Further tumor associated antigens will no doubt continue to be discovered over time. Secondly, following the identification of the antigen/antigens, it is necessary to deliver the antigens in an immunogenic form to the immune system. To generate the cellular immune response critical for tumour rejection, this means the proteins must either be delivered inside the cytoplasm of a host cell (a difficult task for high molecular weight protein antigens) or synthesized by the host cells themselves after gene delivery or DNA immunisation. Viral vectors which have been considered for this purpose include vaccinia, adenoviruses, or retroviruses.

The cell-type which is now widely recognised as providing the optimal immune stimulus is the dendritic cell (DC; see for example Girolomoni and Ricciardi-Castagnoli, 1997). Indeed the DC appears to be the only cell-type capable of stimulating a primary immune response in vivo, and moreover has even been shown to be capable of breaking established tolerance in certain circumstances. A number of groups are exploring the use of DCs in autologous adoptive immunotherapy protocols to stimulate immune responses against tumours in the hope that they may show a therapeutic effect. Such protocols involve culture and/or enrichment of DCs from peripheral blood, in vitro loading of DCs with antigen and reintroduction of the DCs to the patient or direct in vivo loading of DCs with antigen. However this approach has been hampered by the absence of efficient means by which to load these cells with antigens. Recent work has however shown that presentation of antigens by peptide pulsed DCs has produced anti-tumour responses in vivo (Celluzzi et al., 1996; Zitvogel et al., 1996). As regard to viral vectors, retroviruses do not give high efficiency gene delivery to dendritic cells (Reeves et al., 1996; Aicher et al., 1997), and in our hands, unlike work reported by others (Arthur et al., 1997), adenoviruses only give low efficiency gene delivery.

We have previously tested and reported that herpes simplex viruses (HSV) can efficiently infect and deliver genes to dendritic cells (Coffin et al., 1998; WO 00/08191). HSV has a number of advantages over other vector systems for this purpose, in that it can efficiently infect a wide variety of cell-types (including some very hard to infect with other vector systems e.g. Dilloo et al., 1997; Coffin et al., 1998), is easy to manipulate, and can accept large DNA insertions allowing the expression of multiple genes (reviewed by Coffin and Latchman 1996). Delivery of multiple antigens to dendritic cells ex vivo followed by re-introduction into the body or direct administration of antigens to dendritic cells in vivo may be particularly promising approaches to the treatment of some cancers and infectious diseases.

WO 00/08191 teaches that wild type herpes simplex viruses prevent antigen processing occurring in infected dendritic cells and that herpes viruses that either lack both functional UL43 and vhs genes or contain mutations that minimise immediate early gene expression are capable of efficiently infecting dendritic cells without preventing antigen processing occurring in the infected cells.

SUMMARY OF THE INVENTION

We have now surprisingly found that disruption of the gene encoding the virion host shut-off protein (vhs) in HSV vectors enables efficient dendritic cell activation to occur in HSV infected cells. Disruption of the UL43 gene is not also needed. It has previously been shown that HSV infected dendritic cells usually do not become activated either by infection itself, or by other stimuli (Salio et al 1999, Kruse et al 2000).

We have identified a previously unknown function of the vhs protein in preventing dendritic cell activation. Dendritic cell activation is defined as the up-regulation of certain cell surface markers as compared to the non-activated state. These markers include CD83 and CD86. Dendritic cell activation may be stimulated by treatment with lipopolysaccharide (LPS). LPS treatment of dendritic cells infected with HSV does not result in the up-regulation of CD83 or CD86. We have shown that LPS treatment of dendritic cells infected with a mutant HSV in which vhs is inactivated but which have a functional UL43 gene up-regulates both CD83 and CD86. Up-regulation of CD83 and CD86 is not observed following LPS treatment of dendritic cells infected with viruses comprising a functional vhs gene. Thus our results indicate that, for transduced dendritic cells to maximally stimulate an immune response following herpes virus infection, the gene encoding vhs should be disrupted but the gene encoding UL3 need not be.

Our results also demonstrate a role for vhs in the pathogenesis of wild type herpes simplex viruses. HSV infects dendritic cells at a high efficiency and it would seem likely that the reason it has evolved to do this as a part of its natural life-cycle is so that it can minimise a cell-mediated immune response which might otherwise prevent a latent HSV infection being efficiently established or result in clearance of the virus during repeated cycles of latency and reactivation. Dendritic cell activation is important in the stimulation of an effective cell-mediated immune response. Vhs is a virion protein and so, whilst HSV genes are generally not expressed at high levels in dendritic cells, the vhs protein would be delivered to the dendritic cell along with the incoming virus. Thus the novel function of vhs in preventing activation of dendritic cells infected with HSV is likely to be an important function of vhs in the HSV lifecycle following infection of a human with HSV.

Acordingly, the present invention provides a method of stimulating an immune response in a human or animal subject, which methods comprises administering to a subject in need thereof an effective amount of an attenuated herpes virus which:

(i) lacks a functional vhs gene, or a functional equivalent thereof; and (ii) comprises a functional UL43 gene, or functional equivalent thereof; such that dendritic cells are infected with said virus.

Preferably said virus is a human herpes simplex virus. More preferably, said virus is HSV1 or HSV2. The dendritic cells may be infected in vitro or in vivo.

The virus may contain one or more additional mutation. The additional mutations preferably minimise the toxicity of the virus. Typically such mutations result in reduced or minimised immediate early (IE) gene expression. Prevention or reduction of IE gene expression prevents or reduces virus replication. Such mutations include, for example, inactivating mutations in the genes encoding ICP4, ICP27, ICP0 and/or ICP22, preferably ICP27 and/or ICP4. An inactivating mutation in the vmw65-encoding gene removing its transactivating function may also be included (e.g. vmw65 mutations as in Ace et al., 1989 or Smiley et al 1997). Preferably the additional mutations may also minimise the immune response-inhibitory activity of the virus. Such mutations include inactivation of the gene encoding ICP47.

BRIEF DESCRIPTION OF THE DRAWINGS

FIG. 1 shows the viral strains 1764/27-/4-, 1764/27-/4-/pR20.5/vhs, 1764/27-/4-/pR20.5/vhs/HBS-Ag and wild type HSV strain 17+.

FIG. 2 shows the results of FACS analysis to determine the levels of cell-surface expression of CD40, CD80, CD83 and CD86 on un-stimulated (FIG. 2A) and LPS stimulated (FIG. 2B) mock infected cells and cells infected with $17^+$, 1764/27-/4- and 1764/27-/4-/pR20.5/vhs viral strains.

FIG. 3 shows the results of ELISA analysis to determine the effect of viral infection on IL-6 and TNFα secretion from uninfected dendritic cells and dendritic cells infected with $17^+$, 1764/27-/4- and 1764/27-/4-/pR20.5/vhs viral strains.

FIG. 4 shows the proliferative responses of T-cells prepared from hepatitis-B vaccinated and un-vaccinated individuals in response to HBS-Ag. Dendritic cells taken from each individual were either untreated, mixed with recombinant HBS-Ag protein (HBSAg*), infected with the control vector (1764/27-/4-/pR20.5/vhs HBSAg) or infected with the vector expressing HBS-Ag (1764/27-/4-/pR20.5/vhs/HBS-Ag) before mixing with the T cells.

DETAILED DESCRIPTION OF THE INVENTION

A. Viruses

A virus of the invention is capable of infecting dendritic cells without preventing the infected dendritic cells from being activated. Preferably dendritic cells infected with a virus of the invention at a multiplicity of infection (MOI) of 1 can be activated by treatment with LPS or other activation stimuli.

A virus of the invention does not prevent the activation of dendritic cells. To determine when a virus allows the activation of dendritic cells to occur, dendritic cells are infected with the virus at a MOI≧1 and infected dendritic cells are treated with LPS. The levels of cell surface markers such as CD83 and/or CD86 which are up-regulated on activation of dendritic cells may be monitored to determine dendritic cell activation, for example by FACS analysis. The level of these markers on the cell surface will be significantly higher in LPS treated dendritic cells than in cells which have not been treated with LPS if the virus with which the cells are infected allows dendritic cell activiation to occur. Some or all of these markers will also be higher on dendritic cells which have been infected with a virus that allows dendritic cell activation to occur compared to uninfected dendritic cells. If a herpes simplex virus which does not contain an inactivating mutation in vhs is used to infect dendritic cells, significantly less up-regulation of these markers is observed.

To permit activation of infected dendritic cells to occur, a virus of the invention will lack a functional gene encoding vhs (in HSV) or homologues or functional equivalents thereof in other viral species. In addition, a virus of the invention will have a functional UL43 gene. Additional mutations may be made to reduce further the immune-response-inhibitory effects of the virus for example by the inclusion of a mutation in the gene encoding ICP47.

An attenuated virus of the invention is preferably capable of infecting dendritic cells such that minimal toxicity results. Preferably cell survival post-infection will be at least 50% at one day post-infection, more preferably at least 60, 70, 80 or 90% at one day post-infection. To achieve reduced toxicity one or more mutations which reduce viral replications may be included in a virus of the invention. For example, a mutation in the gene encoding VMW65 which mutation minimises the trans-activating activity of the protein and/or a mutation in one or more regulatory immediate early gene such as ICP4, ICP27, ICP0 and ICP22 may be included. Thus a virus of the invention may typically lack functional vhs, ICP27, ICP4 genes and comprise a VMW65 gene which encodes a protein which does not exhibit transcriptional-activation activity, or may typically lack functional vhs, ICP47 and ICP4 genes.

For direct use in vivo some degree of replication competence may typically be beneficial in boosting the immune responses induced. Thus in these circumstances, a virus of the invention preferably lacks a functional vhs gene and may also lack one or more functional genes which are necessary for full pathogenicity of the virus but which are not necessary for viral replication. Such genes include those encoding ICP34.5, ICP6, thymidine kinase and glycoproteins such as gH. Preferably, however, the gene encoding thymidine kinase is functional as mutation of this gene would render the virus insensitive to anti-viral agents such as acyclovir.

Although the present invention has been exemplified using herpes simplex viruses, it will be understood that other viruses of the herpesviridae family may be modified to reduce the prevention of dendritic cell activiation of infected dendritic cells. In particular, such viruses may include varicella zoster virus, pseudo-rabies virus or bovine herpes viruses.

When the virus of the invention is a herpes simplex virus, the virus may be derived from, for example, HSV1 or HSV2 strains, or derivatives thereof, preferably HSV1. Derivatives include inter-type recombinants containing DNA from HSV1 and HSV2 strains. Such inter-type recombinants are described in the art, for example in Thompson et al (1988) and Meignier et al (1988). Derivatives preferably have at least 70% sequence homology to either the HSV1 or HSV2 genomes, more preferably at least 80%, even more preferably at least 90 or 95%, typically as measured by the methods described herein. More preferably, a derivative has at least 70% sequence identity to either the HSV1 or HSV2 genome, more preferably at least 80% identity, even more preferably at least 90%, 95% or 98% identity.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Derivatives which may be used to obtain the viruses of the present invention include strains that already have mutations in genes which it is desired to functionally inactivate in a virus of the invention, for example vhs inactivated strains (as in Jones et al. 1995), ICP47 inactivated strains (as in Goldsmith et al. 1998), strain d120 which has a deletion in ICP4 (DeLuca et al., 1985), strain d27-1 (Rice and Knipe, 1990) which has a deletion in ICP27) or strain d92 which has deletions in both ICP27 and ICP4 (Samaniego et al., 1995). Use of these strains will reduce the number of steps required to produce the mutant HSV strains of the present invention.

The terminology used in describing the various HSV genes is as found in Coffin and Latchman, 1996.

Where gene homologues of the HSV genes described above exist in other herpes virus species, then these homologues will be modified. By a "homologue" it is meant a gene which is functionally equivalent to a HSV gene a homologue typically exhibits sequence homology, either amino acid or nucleic acid sequence homology, to the corresponding HSV gene. Typically, a homologue of an HSV gene will be at least 15%, preferably at least 20%, more preferably at least 30%, 40% or 50% identical at the amino acid level to the corresponding HSV gene.

The geen encoding vhs is the UL41 gene in HSV1 and HSV2. In HSV1 strain 17+ (EMBL accession No. HE1CG) the UL41 gene is from nucleotide 91,170 to nucleotide 92,637. In HSV2 strain HG52 (EMBL accession No. z86099) the UL41 gene is from nucleotide 91,800 to nucleotide 93,275.

Methods of measuring nucleic acid and protein homology are well known in the art. For example the UWGCG Package provides the BESTFIT program which can be used to calculate homology (for example used on its default settings) (Devereux et al. (1984) *Nucleic Acids Research* 12, p387-395). The PILEUP and BLAST algorithms can be used to calculate homology or line up sequences (typically on their default settings), for example as described in Altschul (1993) J. Mol. Evol. 36:290-300; Altschul et al. (1990) J. Mol. Biol. 215: 403-10.

Software for performing BLAST analyses is publicly available through the National Centre for Biotechnology Information (http://www. ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci*. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci*. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Homologues of HSV genes can be identified in a number of ways, for example by probing genomic or cDNA libraries made from other viruses with probes comprising all or part of the HSV gene under conditions of medium to high stringency (for example 0.03M sodium chloride and 0.03M sodium citrate at from about 50° C. to about 60° C.). Alternatively, species homologues may also be obtained using degenerate PCR which will use primers designed to target sequences within the variants and homologues encoding conserved amino acid sequences. The primers will contain one or more degenerate positions and will be used at stringency conditions lower than those used for cloning sequences with single sequence primers against known sequences (for example 0.03M sodium chloride and 0.03M sodium citrate at about 40° C.).

A homologue in a herpes virus is a functional equivalent of an HSV protein if it shares one ore more functional characteristics with the HSV protein. For example, a vhs protein plays a role in reducing protein expression levels in an infected cell by reducing the stability of mRNA. Therefore, a functional equivalent of vhs protein preferably plays a role in shutting down host-cell gene expression by reducing the stability of mRNA. More preferably, a functional equivalent of vhs prevents dendritic cell activation in response to stimuli which activate un-infected dendritic cells.

For reasons of safety, the viruses of the invention are attenuated, typically so that they are incapable of causing disease Viral regions altered for the purposes of attenuation may be either eliminated (completely or partly), or made non-functional, or substituted by other sequences, in particular by a heterologous gene sequence. Attenuating mutations have been described for all viral groups used as viral vectors.

For example, HSV may be rendered avirulent by mutations in ICP34.5 and/or essential genes such as ICP4, ICP27 and/or the vhs gene itself.

Particularly preferred attenuated viruses include viruses which, in addition to lacking a functional gene encoding vhs and optionally lacking a functional ICP47 gene, lack a functional ICP34.5 gene and a functional ICP27 gene and optionally lacks a functional ICP4 gene and/or a VMW65 gene which encodes a protein which has transcriptional-activation activity, and viruses which have a functional ICP27 gene but lack a functional ICP4 gene and a functional ICP34.5 gene and optionally lacks a VMW65 gene which encodes a protein which has transcriptional-activation activity. Such viruses are described in WO98/04726 and WO99/60145, the disclosures of which are herein incorporated by reference.

When a herpes simplex virus of the invention lacks a particular functional essential gene, for example a gene encoding ICP4 or ICP27, the virus is propagated using a cell line expressing that essential gene. For example, when the virus lacks a functional ICP27 gene, the virus may be propagated using V27 cells (Rice and Knipe, 1990), 2-2 cells (Smith et al., 1992) or B130/2 cells (WO98/30707), preferably B130/2 cells. When the virus lacks a functional ICP4 gene the virus may be propagated using a cell line expressing ICP4, for example E5 cells (DeLuca et al., 1985). When the virus lacks a functional ICP4 gene and a functional ICP27 gene the virus is propagated using a cell line expressing both ICP4 and ICP27 (such as E26 cells; Samaniego et al., 1995), and when the virus additionally lacks a functional vmw65 gene the virus may be propagated using a cell line also containing a non-HSV homologue of vmw65 (e.g. equine herpes virus gene 12 or BTIF from bovine herpes virus).

B. Methods of Mutation

The various viral genes referred to may be rendered functionally inactive by several techniques well known in the art. For example, they may be rendered functionally inactive by deletion(s), substitution(s) or insertion(s), preferably by deletion. A deletion may remove portions of a gene or the entire gene. For example, deletion of only one nucleotide may be made, resulting in a frame shift. However, preferably larger deletions are made, for example from 2, 3 or 5 to 10, 20, 30, 50, 100 or 200 nucleotide substitutions. Preferably at least 25%, more preferably at least 50% of the total coding and non-coding sequence (or alternatively, in absolute terms, at least 10 nucleotides, more preferably at least 100 nucleotides, most preferably, at least 1000 nucleotides) is deleted or substituted. It is particularly preferred to remove the entire gene and some of the flanking sequences. Inserted sequences may include the heterologous genes described below. Mutations may comprise both deletion(s) and insertion(s). For example, an insertion may be made into the site of a deletion. Thus insertion of a heterologous gene into a viral gene may replace part or all of the viral gene. In particular, it is preferred to insert the heterologous gene into vhs, ICP47, ICP27 or ICP4. In the case of the VMW65 gene, the entire gene is not deleted since it encodes an essential structural protein, but an inactivating mutation is typically made which abolishes the ability of VMW65 to activate transcriptionally IE genes (e.g. as in Ace et al., 1989 or Smiley et al., 1997).

Mutations may be made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ or GFP, for screening recombinant viruses by, for example, β-galactosidase activity or fluorescence.

C. Heterologous Genes and Promoters

The viruses of the invention may be modified to carry a heterologous gene/genes. The term "heterologous gene" encompasses any gene. Although a heterologous gene is typically a gene not present in the genome of a herpes virus, a herpes gene may be used provided that the coding sequence is not operably linked to the viral control sequences with which it is naturally associated. The heterologous gene may be any allelic variant of a wild-type gene, or it may be a mutant gene. The term "gene" is intended to cover nucleic acid sequences which are capable of being at least transcribed to produce an RNA molecule, which RNA molecule is preferably capable of being translated to produce a polypeptide or to down-regulate gene expression levels by an anti-sense effect A virus of the invention may optionally include some or all of 5' and/or 3' transcribed but untranslated flanking sequences naturally, or otherwise, associated with the translated coding sequence of a heterologous gene. It may optionally further include the associated transcriptional control sequences normally associated with the transcribed sequences, for example transcriptional stop signals, polyadenylation sites and downstream enhancer elements.

The heterologous gene/genes may be inserted into the viral genome by homologous recombination of HSV strains with, for example, plasmid vectors carrying the heterologous gene/genes flanked by HSV sequences. The heterologous gene/genes may be introduced into a suitable plasmid vector comprising herpes viral sequences using cloning techniques well-known in the art. The heterologous gene/genes may be inserted into the viral genome at any location provided that the virus can still be propagated. It is preferred that the heterologous gene/genes is inserted into a gene resulting in attenuation of the virus. Heterologous genes may be inserted at multiple sites within the virus genome.

The transcribed sequence of the heterologous gene/genes is preferably operably linked to a control sequence permitting expression of the heterologous gene/genes in dendritic cells, preferably mammalian dendritic cells, more preferably human dendritic cells. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene/genes and a signal for termination of transcription. The promoter is selected from promoters which are functional in mammalian, preferably human dendritic cells. The promoter/promoters may be derived from promoter sequences of eukaryotic genes. For example, promoters may be derived from the genome of a cell in which expression of the heterologous gene is to occur, preferably a mammalian dendritic cell or more preferably a human dendritic cell. With respect to eukaryotic promoters, they may be promoters that function in a ubiquitous manner (such as promoters of β-actin, tubulin) or, alternatively, a dendritic cell-specific manner. Viral promoters may also be used, for example the Moloney murine leukaemia virus long terminal repeat (MMLV LTR) promoter or other retroviral promoters, the human or mouse cytomegalovirus (CMV) IE promoters.

Expression cassettes and other suitable constructs comprising the heterologous gene/genes and control sequences can be made using routine cloning techniques known to persons skilled in the art (see, for example, Sambrook et al., 1989, Molecular Cloning—a laboratory manual; Cold Spring Harbor Press).

In addition, any of these promoters may be modified by the addition of further regulatory sequences, for example enhancer sequences (including elements of the HSV LAT region). Chimeric promoters may also be used comprising sequence elements from two or more different promoters described above, for example an MMLV LTR/LAT fusion promoter (Lokensgard et al., 1994) or promoters comprising elements of the LAT region (WO98/30707).

Heterologous genes will typically encode polypeptides of therapeutic use. For example, to promote an immune response specifically against a particular tumour, it will be desirable to transfect dendritic cells with a virus of the invention directing expression of a tumour antigen/antigens. A tumour antigen may be specific to a tumour cell, i.e. present in tumour cells but not in non-tumour cells, or it may be present at higher levels in that tumour cell than in a non tumour cell of that type, for example due to up regulation of expression of the antigen. This will be useful in cancer therapy since an infected dendritic cell of the invention can be used to stimulate the host immune system to react to the tumour-specific or tumour-prevalent antigen/antigens resulting in tumour reduction/regression. In particular, it is preferred that the tumour antigen/antigens is expressed on the surface of the tumour cell, for example a cell surface receptor or cell adhesion protein. Examples of tumour antigens include the MUC-1 gene product (Gendler et al., 1990) which is over expressed in a number of tumours including ovarian cancers, human papillomavirus proteins E6 and E7 which are associated with cervical cancer. MART-I, MAGE-I, gp100 and tyrosinase in melanoma, PSA in prostate cancer, CEA in a number of different types of tumour and Her2neu in various cancers including breast cancer.

Heterologous genes may also encode a polypeptide which is capable of modifying an immune response, for example cytokines (such as α-, β- or γ-interferon, interleukins including IL-1, IL-2, tumour necrosis factor, or insulin-like growth factors I or II) or other immunomodulatory proteins including chemokines such as RANTES and co-stimulatory molecules such as CD80, CD86, CD40 and CD40 ligand.

The heterologous gene may also encode a polypeptide/polypeptides of pathogenic origin so that, for example, a dendritic cell infected with a virus of the invention can be used to stimulate the host immune system to produce an immune response to a pathogen, either prior to infection or after infection of the host by the pathogen. Viruses for use in vaccines may typically comprise heterologous genes that encode antigenic polypeptide(s). Preferably such polypeptides of pathogenic origin are derived from pathogenic organisms, for example parasites, bacteria or viruses. Examples of such antigenic polypeptides include hepatitis C virus antigens, hepatitis B surface or core antigens, papillomavirus antigens, HIV antigens and malaria antigens. Viruses comprising heterologous genes from pathogenic organisms may be used for either or both therapeutic and prophylactic treatment.

Therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus multiple heterologous genes can be accommodated within its genome. For example, from 2 to 6 genes may be inserted into the genome.

There are, for example, at least two ways in which this could be achieved. For example, more than one heterologous gene and associated control sequences could be introduced into a particular HSV strain either at a single site or at multiple sites in the virus genome. It would also be possible to use pairs of promoters (the same or different promoters) facing in opposite orientations away from each other, these promoters each driving the expression of a heterologous gene (the same or different heterologous gene) as described above.

D. Dendritic Cells

Dendritic cells can be isolated/prepared by a number of means, for example they can either be purified directly from peripheral blood, or generated from CD34+ precursor cells for example after mobilisation into peripheral blood by treatment with G-CSF, or directly from bone marrow. From peripheral blood adherent precursors can be treated with a GM-CSF/IL-4 mixture (Inaba et al., 1992), or from bone marrow non-adherent CD34+ cells can be treated with GM-CSF and TNF-α (Caux et al., 1992). DCs can be routinely prepared from the peripheral blood of human volunteers, similarly to the method of Sallusto and Lanzavecchia, 1994, using purified peripheral blood mononeucleocytes (PBMCs) and treating 2 hour adherent cells with GM-CSF and IL-4. These are then depleted of CD19+ B cells and CD3+, CD2+ T cells using magnetic beads (see Coffin et al., 1998). Other methods may also be used for the preparation of dendritic cells.

E. Therapeutic Uses

Viruses of the invention, and dendritic cells infected with viruses of the invention may be used in methods of therapy. In particular, viruses of the invention, and dendritic cells infected with viruses of the invention, which express tumour antigens may be used in methods of treating cancer. Specifically, the, viruses of the invention, and dendritic cells infected with viruses of the invention may be used to inhibit the growth of various tumours in mammals, including humans, such as, for instance, ovarian, cervical and endometrial tumours and carcinomas, for example mammary carcinoma, lung carcinoma, bladder carcinoma and colon carcinoma. Other neoplasms whose growth may be inhibited include sarcomas, for example soft tissue and bone sarcomas, and hematological malignancies such as leukemias. Particular examples of cancers which may be treated using viruses of the invention and/or dendritic cells infected with viruses of the invention which express tumour antigens include melanomas, leukemias, cervical cancers and ovarian cancers. A virus for use in treating cancer typically comprises a heterologous gene encoding a tumour antigen. Administration of such a virus, or dendritic cells infected with such a virus, will typically result in the generation of an immune response to the tumour antigen.

Viruses of the invention, and dendritic cells infected with viruses of the invention, may be used in methods of treating or preventing pathogenic infections, for example parasitic, bacterial or viral infections. A virus for use in treating a pathogenic infection typically comprises a heterologous gene encoding an antigen from the pathogenic organism. Administration of such a virus, or dendritic cells infected with such a virus, will typically result in the generation of an immune response to antigen from the pathogenic organism. Such viral infections include herpes virus infections. Thus, a virus of the invention may be used to induce immune responses to the virus itself, for example in the treatment or vaccination of HSV1 or HSV2 infection. Where a virus is intended for use in the treatment of HSV1 or HSV2, the virus may optionally contain a heterologous gene, which heterologous gene encodes an HSV antigen (which is not under the control of its natural promoter) or an immunomodulatory molecule. The viruses/dendritic cells may be administered prior to infection to stimulate a protective immune response in the host, or after infection to stimulate the host immune system to combat the infection.

F. Administration

The herpes viruses of the present invention may thus be used to deliver therapeutic genes to a human or animal in need of treatment. Delivery of therapeutic genes using the herpes viruses of the invention may be used to treat for example, malignancies and/or pathogenic infections.

The viruses of the invention may be used in a patient, preferably a human patient, in need of treatment. A patient in need of treatment is an individual suffering from cancer, or a patient with a pathogenic infection. The aim of therapeutic treatment is to improve the condition of a patient. Typically therapeutic treatment using a virus of the invention allieviates the symptoms of the cancer. A method of treatment of cancer according to the invention comprises administering a therapeutically effective amount of a virus having a functional UL43 gene and lacking a functional vhs gene to a patient suffering from cancer such that the virus is present in dendritic cells in the patient. Administration of virus of the invention to an individual suffering from a tumour will typically kill the cells of the tumour thus decreasing the size of the tumour and/or preventing spread of malignant cells from the tumour.

Typically therapeutic treatment of a pathogenic infection using a virus of the invention alleviates the symptoms of the infection and preferably kills the pathogenic organism. A method of treatment of a pathogenic infection according to the invention comprises administering a therapeutically effective amount of a virus lacking a functional vhs gene to a patient with a pathogenic infection. Preferably the virus enters dendritic cells in the patient or dendritic cells which have been infected with the virus ex vivo are administered to the patient. Prophylactic treatment using a virus of the invention typically leads to the production of antibodies against a tumour antigen or against an antigen from a pathogenic organism in a patient at risk of cancer or a pathological infection. Typically a patient at risk of cancer may be genetically disposed thereto or may have been exposed to or be at risk of exposure to a carcinogen. Typically a patient at risk of a pathogenic infection may be likely to be exposed to a pathogenic organism.

One method for carrying out therapy involves inserting the therapeutic gene/genes into the genome of the herpes virus of the invention, as described above, and then combining the resultant recombinant virus with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, intraperitoneal, subcutaneous or transdermal administration. Subcutaneous or intraperitoneal administration is preferred. Trans- or intradermal administration may be particularly preferred.

Infection of dendritic cells with the virus of the invention may be carried out in vivo by administration of a composition comprising the virus to a patient. The pharmaceutical composition is administered in such a way that the virus containing the therapeutic gene/genes, can infect dendritic cells. The amount of virus administered is in the range of from $10^4$ to $10^{10}$ pfu, preferably from $10^5$ to $10^8$ or from $10^5$ to $10^9$ pfu, more preferably about $10^6$ to $10^8$ pfu. When injected intradermally or trans-dermally administered, for example using a needle-free device, typically from 10 µl to 1 ml, preferably from 100 µl to 1 ml of virus in a pharmaceutically acceptable suitable carrier or diluent or in a particulate composition is administered Another method involves isolating/preparing dendritic cells from peripheral blood or bone marrow and infecting the cells with the virus of the invention in vitro. Transduced dendritic cells are then typically administered to the patient by intramuscular, intraperitoneal, subcutaneous or intravenous injection, or by direct injection into the lymph nodes of the patient, preferably by subcutaneous, intraperitoneal or direct injection into the lymph nodes. Typically from $10^5$ to $10^9$ transduced dendritic cells, preferably from $10^6$ to $10^8$ cells, more preferably about $10^7$ cells are administered to the patient.

The routes of administration and dosages described are intended only as a guide since a skilled practitioner will be able to determine readily the optimum route of administration and dosage for any particular patient. The dosage may be determined according to various parameters, especially according to, for example, the age, weight and condition of the patient.

The following Examples illustrate the invention.

EXAMPLES

Materials and Methods

Construction and Growth of Viral Strains

All virus strains are derived from HSV1 strain 17+, the nucleotide sequence of which is deposited in GenBank (Accession No. HE1CG). Viral strains were produced and propagated using BHK C-21 cells (ECACC No. 8501143) or BHK cells stably transfected with the genes encoding HSV1 ICP27, ICP4 and equine herpes virus gene 12 (Thomas et al. 1999).

For viruses with mutations in VMW65, 3 mM hexamethylene-bisacetamide (HMBA) was included in the media used for virus growth (McFarlane et al., 1992). The following viral strains were used.

(i) 17+ (wild type HSVI)

(ii) 17+/pR20.5/UL43

A cassette from plasmid pR20.5 (Thomas et al. 1999b) consisting of an RSV/lacZ/pA sequence and a CMV/GFP/pA sequence in opposite back-to-back orientations and separated by an HSV LAT region sequence (nts 118,866-120,219) was inserted into the UL43 locus by homologous recombination with purified genomic HSV1 strain 17+ DNA by standard methods. The pR20.5 cassette was first inserted into a plasmid containing UL43 flanking regions (Coffin et al, 1996) at the unique NsiI site, giving plasmid pR20.5/43. The 20.5 cassette can be excised from its pGEM5 (Promega) plasmid backbone with SrfI as an oligonucleotide encoding SrfI was inserted on either side of the cassette. The RSV promoter was excised from pRc/RSV (Invitrogen), lacZ/pA from pCH110 (Pharmacia), CMV/pA from pcDNA3 (Invitrogen) and GFP from pEGFP-N1 (Clontech) for the construction of plasmid pR20.5.

(iii) 1764/27-/4

Virus strain 1764/27-/4- was constructed by recombination of virus strain 1764/27-/4-/pR20.5 DNA with empty ICP4 flanking regions and the selection of virus plaques which do not express GFP or lacZ. Virus strain 1764/27-/4-/pR20.5 is described in Thomas et al. 1999b and contains the pR20.5 cassette inserted into the ICP4 geneso as to replace the gene encoding ICP4 of a virus also deleted for ICP27 and ICP34.5 and with an inactivating mutation in the gene encoding VMW65.

(iv) 1764/27-/4-/pR20.5/vhs

Virus strain 1764/27-/4-/pR20.5/vhs was constructed by insertion of the pR20.5 cassette into vhs flanking regions at the unique NruI site in the vhs encoding gene of HSV1 strain 17+ and the resulting plasmid (pR20.5/vhs) was recombined into HSV strain 1764/27-/4- DNA. Virus strain 1764/27-/4-/pR20.5/vhs is therefore deleted for the genes encoding ICP4, ICP27 and ICP34.5, and has inactivating mutations in the genes encoding vmw65 and vhs.

(v) 1764/27-/4-/pR19lacZ

Virus strain 1764/27-/4-/pR19lacZ was constructed as for virus (iv) above except the pR19lacZ cassette (Wagstaff et al. 1998) was recombined into the latency associated transcript (LAT) region of virus strain 1764/27-/4- rather than the pR20.5 cassette into vhs.

(vi) 1764/27-/4-/pR20.5/vhs/HBS-Ag

The lacZ gene in the pR20.5/vhs plasmid was replaced by the gene encoding hepatitis surface antigen (HBS-Ag) by digestion of pHBV130 (Gough and Murray, 1982) with XhoI and NsiI and insertion of the fragment released into pSP72 (Promega) between the SalI and SmaI sites. pR20.5/vhs was digested with XbaI and EcoRI to release the lacZ gene which was replaced by the HBS-Ag gene excised from pSP72 with HindIII and EcoRI. The resulting plasmid was recombined into 1764/27-/4-/pR20.5/vhs viral DNA and non-lacZ expressing plaques selected and purified. Genome structure was then confirmed by Southern blot.

Dendritic Cell Preparation

DC were prepared from peripheral blood as previously described (Coffin et al 1998). Briefly, peripheral blood mononuclear cells (PBMCs) were prepared from 60 ml of healthy/hepatitis B vaccinated donor blood using lymphoprep (Nycomed). After removal of red cells, non-adherent cells (mainly T cells and B cells) were removed, washed in HBSS and centrifuged at 1400 rpm, 5 minutes, RT. The cell pellet was resuspended in a 2 ml 90% FCS:10% dimethylsulphoxide (DMSO) mix, aliquoted and stored at −80 C for subsequent T cell isolation. Adherent cells were cultured in RPMI medium supplemented with GM-CSF (0.1 µg/ml) and IL-4 (0.05 µg/ml) and incubated for 7 days, at 37 C, 5% $CO_2$. After further lymphoprep purification cells were then magnetically depleted using anti-CD19, anti-CD2 (Harlan) and anti-CD3 (Harlan) antibodies and DC were resuspended in complete RPMI medium for immediate use.

Isolation of CD4+ T-cells

T and B cell frozen as above were defrosted quickly, washed in HBSS and centrifuged at 1400 rpm, for 5 minutes. Cells were resuspended in 2 ml complete RPMI medium, counted and incubated with anti-CD19 (BU12-200 µl neat, Immunology dept, UCL), anti-CD14 (HB246-200 µl neat, Immunology dept, UCL) and anti-HLA-DR (L243-100 µl neat, Immunology dept, UCL) mAb and left on ice for 30 minutes. The cells were washed in HBSS, resuspended in 2 ml complete RPMI medium, mixed with sheep anti-mouse antibodies bound to magnetic beads (Dynabeads, Dynal) at a ratio of 10 µl beads/$10^6$ contaminating cells and incubated on a rotor mixer at 4 C, for 45 minutes. CD4+ T cells were then depleted by removing the supernatant after placing the cell suspension/magnetic bead mix in contact with a magnet, for 10 minutes, on ice. CD4+ T cells were counted, resuspended in complete RPMI medium at the appropriate concentration, left on ice or cultured o/n at 37 C, 5% $CO_2$ for subsequent use.

Infection of DC

DC were pelleted at 1400 rpm for 5 minutes at room temperature. DC were then infected at MOI of 1 by resuspension in RPMI medium containing virus for 1 hour at 37 C, 5% $CO_2$. 1 ml of RPMI supplemented with GM-CSF (0.1 µg/ml) and IL-4 (0.05 µg/ml) was then added and DC incubated at 37 C, 5% $CO_2$. For LPS stimulation, RPMI additionally containing 100 ng/ml LPS was used.

Cytokine Analysis

IL-6, and TNF-α were measured in DC culture supernatants using commercially available ELISA kits (R&D Systems). Prior to ELISA, supernatants were collected 42 hours post-infection of DC with the indicated viruses and stored at −20 C before use.

T Cell Proliferation Assays

DC and CD4+ T cells were isolated and treated as above from hepatitis B vaccinated and un-vaccinated human individuals. DC were used at dilutions from $1 \times 10^5$ DC/ml to $1 \times 10^4$ DC/ml and CD4+ T cells at $1 \times 10^6$ cells/ml. Experiments at each of DC concentration were performed in triplicate. 100 µl of DC and 100 µl of CD4+ T cells were added to each assay well. Where indicated recombinant hepatitis B surface antigen (Austral) was added to wells at a final concentration of 1 µg/well. HSV-1-infected and uninfected DC were cultured with CD4+ T cells for 6 days at 37 C, 5% $CO_2$. 1 µCu/well [$^3$H] thymidine (Amersham) was then added and 18 hours later cells harvested and [$^3$H] thymidine incorporation counted.

Example 1

Preliminary Data Showing That HSV Strains Not Containing a Functional vhs Gene Give Enhanced Activation of Dendritic Cells Following Virus Infection Here in each case $1 \times 10^5$ dendritic cells were infected with each of the viruses by gentle pelleting, resuspension in about 100 µl virus suspension in DMEM, incubation at 37° C. for 1 hr, and transfer into 24 well plates with 2 ml of RPMI/10% FCS+100 ng/ml GM-CSF, 50 ng/ml IL-4. These plates were then incubated at 37° C./5% $CO_2$ overnight. Dendritic cells were also treated with lipopolysaccharide (LPS) a known dendritic cell activator, and untreated as a controls.

Supernatants from these infections and from the control were then used in ELISA tests to detect levels of secreted cytokines. Fluorescence activated cell sorting (FACS) was also used to detect levels of expression of CD86 on the surface of infected and control dendritic cells. In dendritic cell cultures there are two populations of cells with respect to levels of CD86 expression. These are observed as two peaks by FACS analysis reflecting a first peak of cells with a relatively lower level of CD86 expression and a second peak of cells with a relatively higher level of CD86 expression. On activation by e.g. LPS more of the cells express higher levels of CD86 and there are thus more cells are found in the second peak.

Results

TABLE 1

Cytokine concentration in culture supernatants 24 hr after infection with the indicated viruses or in control supernatants at an MOI of 1. Measured by ELISA.

| Treatment | Cytokine Concentration (ng/well) | |
|---|---|---|
| | IL-6 | TNFa |
| 17+/pR20.5/UL43 | 6 | 1.1 |
| 1764/27−/4−/pR19lacZ | 4 | 0.8 |
| 1764/27−/4−/pR20.5/vhs | 46 | 7.1 |
| No infection | 4 | 0.9 |

TABLE 2

Expression of CD86 on control cells and cells infected with the indicated viruses.

| Treatment | % cells peak 1 | % of cells peak 2 | Mean fluorescence intensity peak 2 |
|---|---|---|---|
| 17+/pR20.5/UL43 | 43.35 | 46.85 | $5 \times 10^2$ |
| 17+/pR20.5/UL43 + LPS | 56.93 | 29.06 | |
| 1764/27−/4−/pR19lacZ | 24.1 | 68.5 | $5 \times 10^2$ |
| 1764/27−/4−/pR19lacZ + LPS | 52.71 | 35.32 | $7 \times 10^2$ |
| 1764/27−/4−/pR20.5/vhs | 27.81 | 64.61 | $1 \times 10^3$ |
| 1764/27−/4−/pR20.5/vhs + LPS | 39.52 | 52.40 | $9 \times 10^2$ |
| No infection | 48.95 | 31.45 | $1 \times 10^3$ |
| No infection + LPS | 30.33 | 60.81 | $9 \times 10^2$ |

Conclusions

The results show that untreated dendritic cells secrete minimal levels of the cytokines tested and have the expected "resting" levels of CD86 on their surface. Following LPS treatment cytokine levels are significantly stimulated and the level of surface expression of CD86 increases significantly. In the experiments above the mean fluorescence intensity in LPS treated cells is approximately $1 \times 10^3$ by FACS analysis with an anti-CD86 antibody. These results are indicative that dendritic cells are in an activated state.

Following infection of dendritic cells with the indicated viruses it can clearly be seen that for activation of dendritic cells to occur by these assays the virus must contain an inactivating mutation in the gene encoding vhs. Viruses of varying levels of disablement have been used, and only the virus containing the vhs mutation gives significant activation of the dendritic cells by these assays. It can also be seen that if mutation to vhs is not included when cells are treated with LPS as well as infected with the indicated viruses, CD86 levels are not increased in as many cells as occurs by treatment with LPS alone. Also, unless vhs mutation is included, the mean fluorescence intensity of CD86 expressing cells as measured by FACS following virus infection is reduced from that seen if cells are treated with LPS. For maximum immune stimulation by dendritic cells it can thus be concluded that inactivating mutation(s) in the gene encoding vhs should be included.

Example 2

HSV Strains Not Containing a Functional vhs Protein Do Not Block Dendritic Cell Activation Fluorescence activated cell sorting (FACS) was used to detect levels of expression of CD86, CD80, CD83 and CD40 on the surface of infected and control dendritic cells. Supernatants from the infections was used to assess levels of cytokines by ELISA.

Results

Figure 2A:
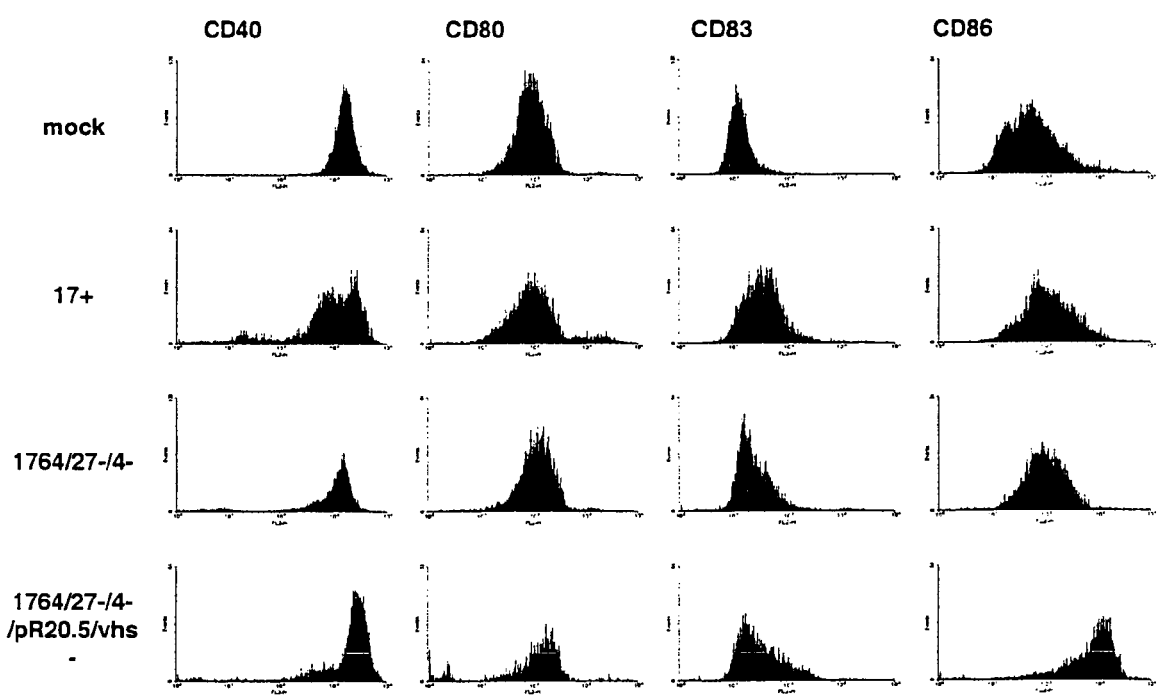
Figure 2B:
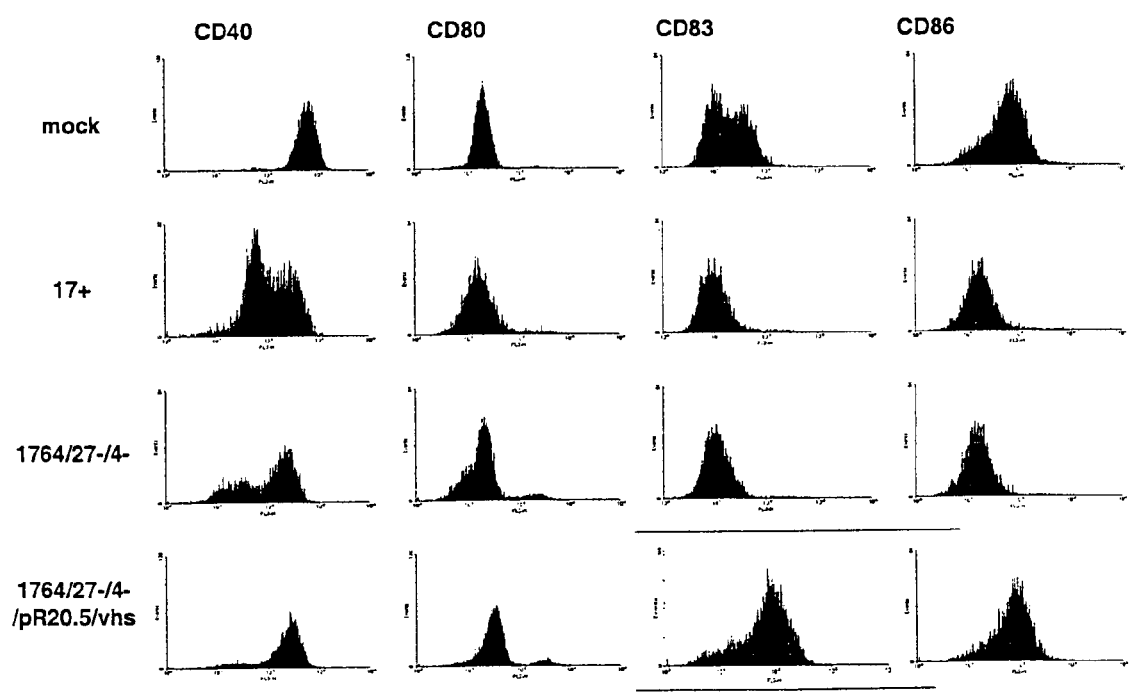
Figure 3:
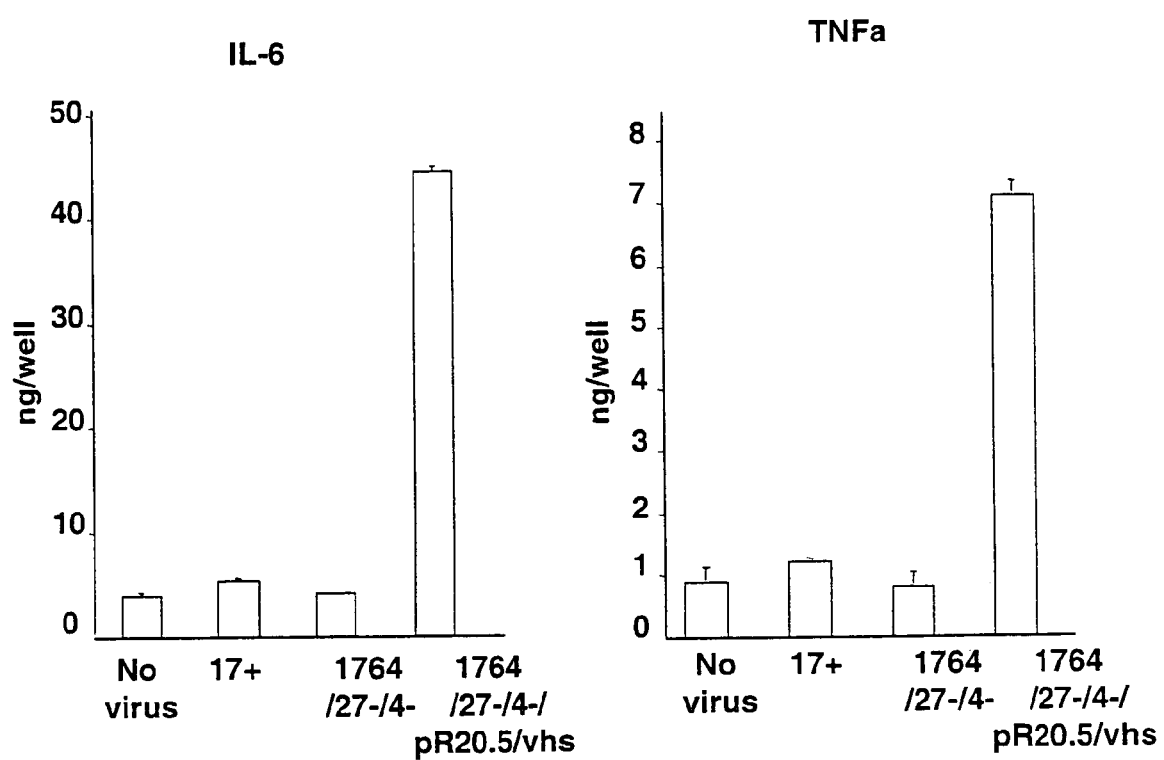
Figure 4:
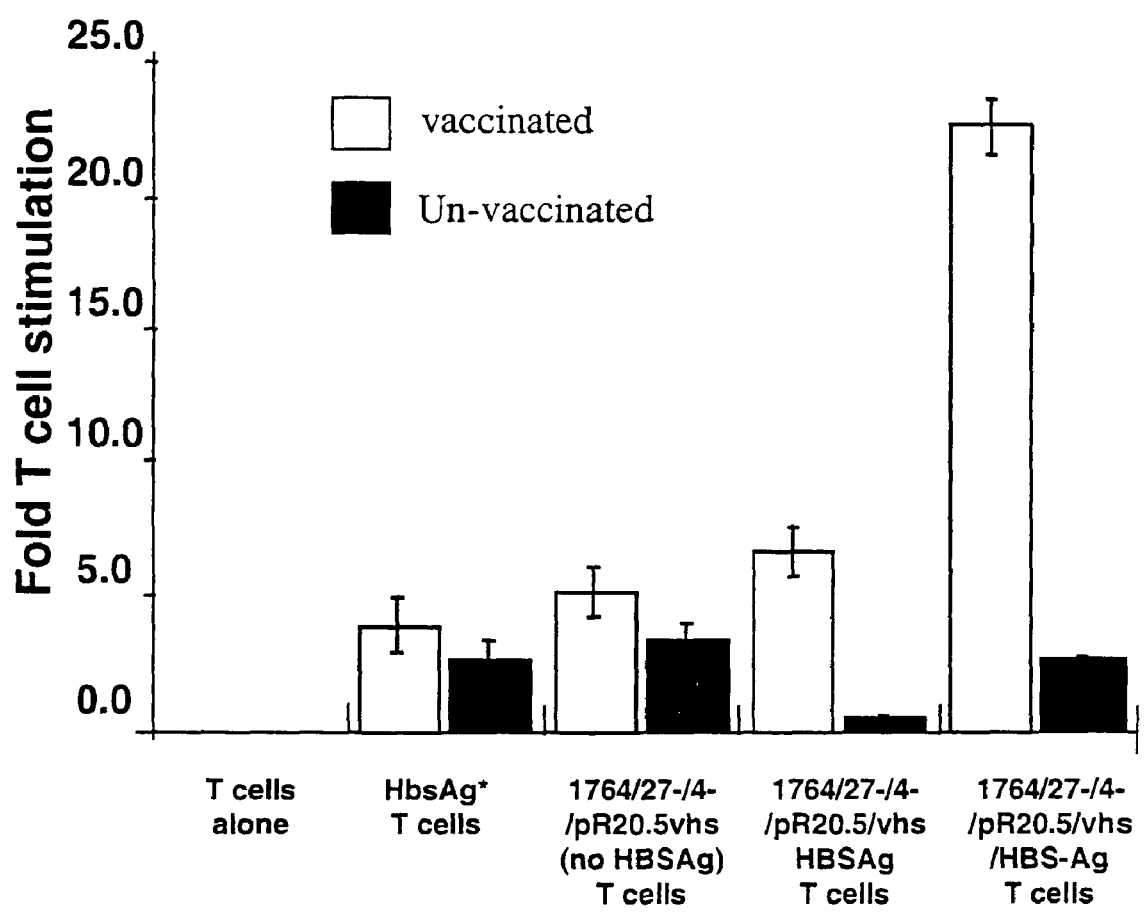

The ELISA results (FIG. 3) show that while DC can be infected with HSV at high efficiency, cytokines indicative of DC activation are not produced with either a wild type (strain 17+) or a disabled (strain 1764/27−/4−) virus. However if vhs is inactivated from strain 1764/27−/4−, giving strain 1764/27−/4−/pR20.5/vhs, cytokines indicative of DC activation are then produced. FACS analysis (FIG. 2) on non-LPS stimulated DC shows that infection with essentially wild type HSV (strain 17+) or a replication incompetent HSV vector (strain 1764/27−/4−) prevents the increased expression of CD86. As discussed above, increased CD86 expression would be expected if DC had become activated by the infection process. CD40 levels are also altered/reduced in HSV infected cells. However, if vhs is inactivated (strain 1764/27−/4−/pR20.5/vhs), CD86 levels are increased indicating activation, and CD40 levels are unaffected. CD80 and CD83 are not greatly affected in unstimulated DC infected with HSV. CD83 (B7.1) and CD86 (B7.2) are two key T-cell co-stimulatory molecules, CD40 is a key T-cell activator, and CD83 is a DC marker up-regulated during DC maturation and activation.

When DC are LPS stimulated at the time of infection effects on CD40 levels are more marked with both wild type (strain 17+) or disabled (strain 1764/27−/4−) virus. If vhs is inactivated, however, these effects on CD40 are prevented. LPS stimulated DC usually significantly up-regulate CD83 and CD86 expression, but this is blocked by HSV (strains 17+ and 1764/27−/4−) unless vhs is inactivated (strain 1764/27−/4−/pR20.5/vhs). When vhs is inactivated, both CD83 and CD86 levels are increased to a similar or greater extent as in LPS stimulated but uninfected cells.

Conclusion

As in the preliminary experiments (Example 1), it can clearly be seen that for dendritic cells to become activated as measured by surface marker expression levels in response to HSV infection or HSV infection and LPS stimulation it is clear that the gene encoding vhs must be inactivated. Viruses encoding functional vhs do not allow dendritic cells to become significantly activated as measured by the expression levels of the surface markers tested.

Example 3

DC Transduced with a vhs Inactivated HSV Vector Direct Antigen Specific T Cell Responses in vitro The results above suggested that HSV vectors in which vhs is inactivated might be used as effective vectors for DC as the inactivating effects of HSV in DC have been prevented. Indeed DC infected with such HSV mutants appear to be specifically activated in response to infection as measured by CD86 up-regulation and the secretion of certain cytokines. To test whether vhs-inactivated HSV mutants might be used to direct antigen specific immune responses following the delivery of antigen encoding genes to DC, experiments were performed using DC and T-cells prepared from hepatitis B vaccinated and un-vaccinated individuals. Here a virus was first constructed in which a hepatitis B surface antigen (HBS-Ag) expression cassette was inserted into the vhs encoding gene of the IE gene deficient virus. T-cell proliferation assays were then performed in which DC from vaccinated or un-vaccinated individuals were either untreated, 'loaded' with antigen by mixing with recombinant HBS-Ag protein, infected with the control marker gene containing vector (1764/27-/4-/pR20.5/vhs at MOI=1), infected with the control vector (1764/27-/4-/pR20.5/vhs at MOI=1) and also mixed with recombinant HBS-Ag, or infected with the vector expressing HBS-Ag (1764/27-/4-/pR20.5/vhs/HBS-Ag at MOI=1). DC were then mixed with T-cells derived from the same vaccinated or unvaccinated individuals respectively, and effects on T-cell proliferation observed in standard T-cell proliferation assays.

These experiments showed (Fig.) that while HBS-Ag recombinant protein and the control HSV vector could induce a small T-cell proliferative response in vaccinated individuals, the HSV response probably indicating proliferation of T-cells specific to HSV structural proteins, and the control vector mixed with recombinant HBS-Ag could illicit a slightly greater response, the HBS-Ag expressing vector gave a significantly greater response than any of these. Thus following delivery of HBS-Ag directly into DC using an HSV vector a significant and specific T-cell proliferative response was induced which did not occur following mixing with recombinant antigen alone. HSV vectors with vhs inactivated thus allow the delivery of antigen coding genes to DC such that DC retain the ability to stimulate antigen specific T-cell proliferative responses.

REFERENCES

Gendler, S. J. et al., (1990), J. Biol. Chem. 265:15286-15293.
Aicher, A. et al., (1997), Exp. Hematol. 25:39-44.
Samaniego, L. A. et al., (1995), J. Virol. 69:5705-5715.
Zitvogel, L. et al., (1996), J. Exp. Med 183:87-97.
Celluzzi, C. M. et al., (1996), J. Exp. Med. 183:283-287.
Reeves, M. E. et al., (1996), Cancer Research 56:5672-5677.
Arthur, J. F. et al., (1997), Cancer Gene Therapy 4:17-25.
Coffin, R. S. et al., (1998), Gene Therapy 5:718-722.
Coffin, R. S. and Latchman, D. S. (1996), Genetic Manipulation of the Nervous System (D. S. Latchman Ed.) pp 99-114: Academic Press, London.
Inaba, K. et al., (1992) J. Exp. Med. 175:1157-1167.
Caux, C. et al., (1992), Nature 360:258-261.
Sallusto, F. and Lanzavecchia, A. (1994), J. Exp. Med. 179: 1109-1118.
Coffin, R. S. et al., (1996), Gene Therapy 3:886-891.
Ace, C. I. et al., (1989), J. Virol. 63:2260-2269.
Smith, I. L. et al., (1992), Virology 186:74-86.
Rice, S. A. and Knipe, D. M. (1990), J. Virol. 64:1704-1715.
DeLuca, N. A. et al., (1985), J. Virol. 56: 558-570.
MacFarlane, M. et al., (1992), J. Gen. Virol. 73:285-292.
Lokensgard, J. R. et al., (1994), J. Virol. 68:7148-7158.
Smiley, J. R. and Duncan, J. (1997), J. Virol. 71:6191-6193.
Thomas, S. K. et al., 1999 J. Viol 73:7399-7409.
Thomas, S. K. et al. 1999b J. Viol 73:6618-6625
Wagstaff, M. J. D. et al. 1998 Gene Therapy 5:1566-1570
Dilloo, D et al. 1997 Blood 89:119-127.
Jones, F. E. et al. 1995 J. Virol 69: 4863-4871
Goldsmith, K et al. 1998 J. Exp Med. 87: 341-348
Salio et al. 1999 Eur. J. Immunol. 29: 3245-3253
Kruse et al 2000 J. Virol. 74, 7127-7136
Gough N. and K. Murray, J. Mol. Biol. 1982. 162, 43-67

I claim:

1. A method of stimulating an immune response in a human or animal subject, which method comprises administering to a subject in need thereof an effective amount of an attenuated herpes virus which:
   (i) lacks a functional vhs gene;
   (ii) lacks a functional gene encoding ICP47; and
   (iii) comprises a functional UL43 gene such that dendritic cells are infected with said virus.

2. The method of claim 1, wherein said virus is a herpes simplex virus 1 or 2.

3. The method of claim 1, wherein said virus lacks at least one further functional immediate early gene.

4. The method of claim 3, wherein said immediate early gene is selected from genes encoding ICP0, ICP4, ICP22 and ICP27.

5. The method of claim 3, wherein said virus lacks both a functional gene encoding ICP27 and a functional gene encoding ICP4.

6. The method of claim 1, wherein said virus comprises a heterologous gene.

7. The method of claim 1, wherein said heterologous gene is operably linked to a control sequence permitting expression of said heterologous gene in a dendritic cell.

8. The method of claim 1, wherein said heterologous gene encodes a polypeptide of therapeutic use.

9. The method of claim 1, wherein said heterologous gene encodes a polypeptide selected from the group consisting of: a polypeptide, the level of expression of which is increased in or on the surface of tumour cells as compared to non-tumour cells; a polypeptide which is present in or on the surface of tumour cells but absent from non-tumour cells; a polypeptide capable of modifying immune responses; and a polypeptide of parasitic, viral or bacterial origin.

10. The method of claim 1, wherein said virus comprises more than one heterologous gene.

11. The method of claim 1, wherein said virus comprises a heterologous gene or genes capable of modulating an immune response.

12. The method of claim 11, wherein said heterologous gene encodes a chemokine, cytokine, or co-stimulatory molecule.

13. The method of claim 1, wherein said subject is a human subject.

14. The method of claim 1, wherein the virus is administered by injection, by infusion, by an intra- or trans-dermal route, or by biolistic means.

15. The method of claim 1, wherein the subject is in need of treatment of or protection against a pathogenic infection.

16. The method of claim 1, wherein the subject is in need of treatment of or protection against cancer.

17. The method of claim 15, wherein the pathogenic infection is HSV1 or HSV2 infection.

18. The method of claim 17, wherein the pathogenic infection is HSV1 infection and the virus is an attenuated HSV1.

19. The method of claim 18, wherein the pathogenic infection is HSV2 infection and the virus is an attenuated HSV2.

* * * * *